(12) United States Patent
Kim et al.

(10) Patent No.: US 9,969,832 B2
(45) Date of Patent: *May 15, 2018

(54) MODIFIED CONJUGATED DIENE-BASED POLYMER, METHOD FOR PREPARING SAME, AND RUBBER COMPOSITION COMPRISING SAME

(71) Applicant: LG Chem, Ltd., Seoul (KR)

(72) Inventors: Jin-Young Kim, Daejeon (KR); No-Ma Kim, Daejeon (KR); Ro-Mi Lee, Daejeon (KR); He-Seung Lee, Daejeon (KR)

(73) Assignee: LG Chem, Ltd. (KR)

( * ) Notice: Subject to any disclaimer, the term of this patent is extended or adjusted under 35 U.S.C. 154(b) by 155 days.

This patent is subject to a terminal disclaimer.

(21) Appl. No.: 14/909,915

(22) PCT Filed: Sep. 25, 2014

(86) PCT No.: PCT/KR2014/008942
§ 371 (c)(1),
(2) Date: Feb. 3, 2016

(87) PCT Pub. No.: WO2015/056898
PCT Pub. Date: Apr. 23, 2015

(65) Prior Publication Data
US 2016/0177011 A1 Jun. 23, 2016

(30) Foreign Application Priority Data

Oct. 17, 2013 (KR) .................. 10-2013-0124244
Sep. 19, 2014 (KR) .................. 10-2014-0125069

(51) Int. Cl.
| | | |
|---|---|---|
| C08F 236/10 | (2006.01) | |
| C08K 3/36 | (2006.01) | |
| C07F 7/18 | (2006.01) | |
| B60C 1/00 | (2006.01) | |
| C08C 19/22 | (2006.01) | |
| C08C 19/25 | (2006.01) | |
| C08K 3/00 | (2018.01) | |
| C08L 15/00 | (2006.01) | |

(52) U.S. Cl.
CPC .......... *C08F 236/10* (2013.01); *B60C 1/0016* (2013.01); *C07F 7/1836* (2013.01); *C08C 19/22* (2013.01); *C08C 19/25* (2013.01); *C08K 3/0033* (2013.01); *C08K 3/36* (2013.01); *C08L 15/00* (2013.01)

(58) Field of Classification Search
CPC ....... B60C 1/0016; C08C 19/22; C08C 19/25; C08K 3/0033; C08K 3/36; C08L 15/00; C08F 236/10; C08F 7/1836
See application file for complete search history.

(56) References Cited

U.S. PATENT DOCUMENTS

| | | | | |
|---|---|---|---|---|
| 5,508,333 A | * | 4/1996 | Shimizu .................. | C08C 19/44 524/423 |
| 9,644,045 B2 | * | 5/2017 | Kim et al. ............... | C08F 8/42 |
| 9,695,256 B2 | * | 7/2017 | Lee et al. ................. | C08F 8/42 |
| 2009/0239974 A1 | | 9/2009 | Mori et al. | |
| 2010/0179274 A1 | | 7/2010 | Jinbo et al. | |
| 2014/0114014 A1 | * | 4/2014 | Tokimune et al. ...... | C08K 3/36 524/547 |
| 2014/0243476 A1 | | 8/2014 | Lee et al. | |
| 2016/0208023 A1 | | 7/2016 | Lee et al. | |
| 2016/0208024 A1 | | 7/2016 | Kim et al. | |

FOREIGN PATENT DOCUMENTS

| | | |
|---|---|---|
| CN | 101160353 A | 4/2008 |
| CN | 101268136 A | 9/2008 |
| EP | 1854839 A1 | 11/2007 |
| EP | 1925636 A1 | 5/2008 |
| EP | 2266819 A1 | 12/2010 |
| JP | H10280275 A | 10/1998 |
| JP | 2010241982 A | 10/2010 |
| JP | 2011093989 A | 5/2011 |
| JP | 2011121906 A | 6/2011 |
| JP | 2016528369 A | 9/2016 |
| JP | 2016530376 A | 9/2016 |
| KR | 20070117626 A | 12/2007 |
| KR | 20080044880 A | 5/2008 |
| KR | 20130090810 A | 8/2013 |
| KR | 20130090811 A | 8/2013 |
| WO | 2013119006 A1 | 8/2013 |
| WO | 2016085102 A1 | 6/2016 |
| WO | 2016085143 A1 | 6/2016 |
| WO | 2016089035 A1 | 6/2016 |

OTHER PUBLICATIONS

Supplementary European Search Report for Application No. EP14853362, dated May 24, 2017.
Database WPI Week 201135 Thomson Scientific, London, GB, AN 2011-F04034, XP002770051.
Database WPI Week 201076, Thomson Scientific, London, GB, AN 2010-N51479, XP002770052.
International Search Report for Application No. PCT/KR2014/008942 dated Jan. 5, 2015.

* cited by examiner

Primary Examiner — Nathan M Nutter
(74) Attorney, Agent, or Firm — Lerner, David, Littenberg, Krumholz & Mentlik, LLP

(57) ABSTRACT

Disclosed are a modified conjugated diene-based polymer represented by Chemical Formula 1, a method of preparing the same, and a rubber composition including the same.

17 Claims, 1 Drawing Sheet

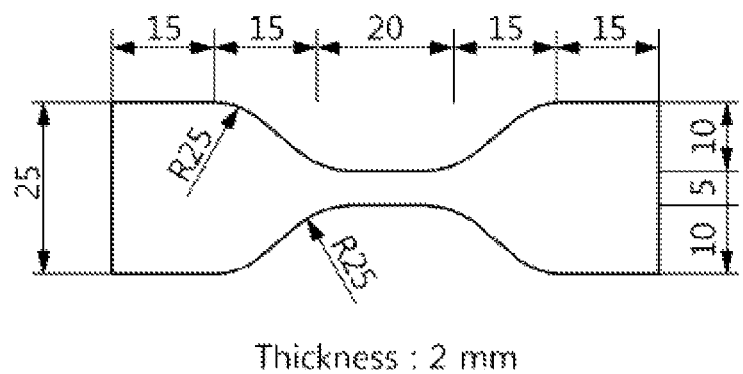

MODIFIED CONJUGATED DIENE-BASED POLYMER, METHOD FOR PREPARING SAME, AND RUBBER COMPOSITION COMPRISING SAME

CROSS-REFERENCE TO RELATED APPLICATION

The present application is a national phase entry under 35 U.S.C. § 371 of International Application No. PCT/KR2014/008942, filed Sep. 25, 2014, which claims priority from Korean Application No. 10-2014-0125069, filed Sep. 19, 2014 and Korean Application No 10-2013-0124244, filed Oct. 17, 2013, all of which are incorporated herein by reference.

TECHNICAL FIELD

The present invention relates to a modified conjugated diene-based polymer, a method of preparing the same, and a rubber composition comprising the same. More particularly, the present invention relates to a modified conjugated diene-based polymer having high compatibility with an inorganic filler, processability, tensile strength, wear resistance, and wet skid resistance, a method of preparing the same, and a rubber composition comprising the same.

BACKGROUND ART

The demand for stability and durability of vehicles is continuously increasing. Accordingly, there is a need to develop rubber exhibiting excellent wet skid resistance and mechanical strength and low rolling resistance, as a material for vehicle tires, especially tire treads, which are in contact with roads.

Conventional tire treads have been formed by mixing conjugated diene-based rubber with an inorganic filler for enhancing the above properties, but suffer from problems of high hysteresis loss and low dispersibility.

DISCLOSURE

Technical Problem

An object of the present invention is to provide a modified conjugated diene-based polymer having high processability and superior compatibility with an inorganic filler.

Another object of the present invention is to provide a method of preparing the modified conjugated diene-based polymer.

Still another object of the present invention is to provide a rubber composition, which includes the modified conjugated diene-based polymer and has improved heat build-up and high tensile strength, wear resistance, fuel economy, and wet skid resistance.

Yet another object of the present invention is to provide a tire including the rubber composition.

Still yet another object of the present invention is to provide a modifier for use in preparing the modified conjugated diene-based polymer.

Technical Solution

In order to accomplish the above objects, an aspect of the present invention provides a modified conjugated diene-based polymer represented by Chemical Formula 1 below:

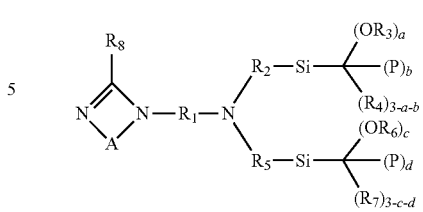

Chemical Formula 1 in Chemical Formula 1, $R_1$, $R_2$, and $R_5$ are each independently a C1-C10 alkylene group, $R_3$, $R_4$, $R_6$, and $R_7$ are each independently a C1-C10 alkyl group, $R_8$ is hydrogen or a C1-C10 alkyl group, P is a conjugated diene-based polymer chain, P is a conjugated diene-based polymer chain, a and c are each independently 0, 1, or 2, b and d are each independently 1, 2, or 3, a+b and c+d are each independently 1, 2, or 3, and A is

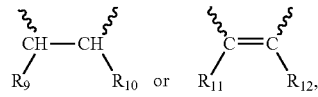

wherein $R_9$, $R_{10}$, $R_{11}$, and $R_{12}$ are each independently hydrogen or a C1-C10 alkyl group.

Another aspect of the present invention provides a method of preparing a modified conjugated diene-based polymer, comprising: (a) polymerizing a conjugated diene monomer, or a conjugated diene monomer and a vinyl aromatic monomer, with an organometallic compound in the presence of a solvent, thus forming an active polymer having a metal end; and (b) modifying the active polymer with a compound represented by Chemical Formula 8 below:

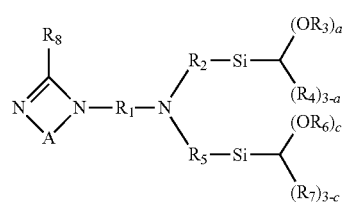

Chemical Formula 8 in Chemical Formula 8, $R_1$, $R_2$, and $R_5$ are each independently a C1-C10 alkylene group, $R_3$, $R_4$, $R_6$, and $R_7$ are each independently a C1-C10 alkyl group, $R_8$ is hydrogen or a C1-C10 alkyl group, a and c are each independently 0, 1, or 2, and A is

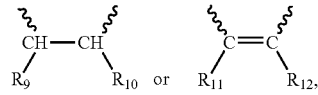

wherein $R_9$, $R_{10}$, $R_{11}$, and $R_{12}$ are each independently hydrogen or a C1-C10 alkyl group.

Still another aspect of the present invention provides a modified conjugated diene-based polymer rubber composition, comprising 100 parts by weight of the modified conjugated diene-based polymer and 0.1 to 200 parts by weight of an inorganic filler.

Yet another aspect of the present invention provides a modifier for use in preparing the modified conjugated diene-based polymer.

Still yet another aspect of the present invention provides a tire using the modified conjugated diene-based polymer rubber composition.

Advantageous Effects

According to an embodiment of the present invention, a modified conjugated diene-based polymer having high processability and superior compatibility with an inorganic filler can be provided. Also, a rubber composition including the modified conjugated diene-based polymer can be utilized to manufacture a tire having improved heat build-up and high tensile strength, wear resistance, fuel economy and wet skid resistance, as well as low rolling resistance.

DESCRIPTION OF DRAWING

The FIGURE illustrates the size of a test sample for tensile testing of the rubber composition according to the present invention.

BEST MODE

Hereinafter, a detailed description will be given of the present invention. Prior thereto, the terms or words used in the description and the claims of the present invention are not to be construed limitedly as having typical or dictionary meanings and should be interpreted as having the meanings and concepts of the invention in keeping with the scope of the invention based on the principle that the inventors can appropriately define the terms in order to describe the invention in the best way.

Therefore, the examples described in the present specification are merely preferred embodiments of the present invention, and do not represent all of the technical ideas of the present invention, and thus, it is to be understood that a variety of equivalents and modifications able to substitute therefor may be provided at the point of time at which the present invention is filed.

According to an aspect of the present invention, a modified conjugated diene-based polymer is represented by Chemical Formula 1 below:

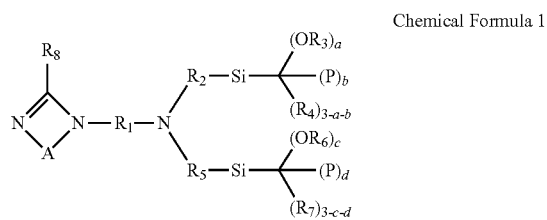

Chemical Formula 1 in Chemical Formula 1, $R_1$, $R_2$, and $R_5$ are each independently a C1-C10 alkylene group, $R_3$, $R_4$, $R_6$, and $R_7$ are each independently a C1-C10 alkyl group, $R_8$ is hydrogen or a C1-C10 alkyl group, P is a conjugated diene-based polymer chain, a and c are each independently 0, 1, or 2, b and d are each independently 1, 2, or 3, and a+b and c+d are each independently 1, 2, or 3.

Also in Chemical Formula 1, A is a bivalent linking group, which may be connected to both nitrogen atoms, and includes an alkylene group such as

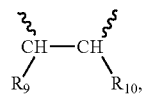

or an alkenylene group such as

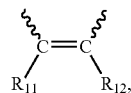

wherein $R_9$, $R_{10}$, $R_{11}$, and $R_{12}$ are each independently hydrogen or a C1-C10 alkyl group.

The modified conjugated diene-based polymer has a number average molecular weight (Mn) of 1,000 to 2,000,000 g/mol, preferably 10,000 to 1,000,000 g/mol, and more preferably 100,000 to 1,000,000 g/mol. When the number average molecular weight of the modified conjugated diene-based polymer falls in the above range, a modification reaction may efficiently occur, and desired properties may be obtained.

The modified conjugated diene-based polymer has a polydispersity index (Mw/Mn) of 0.5 to 10, preferably 0.5 to 5, and more preferably 1 to 4. When the polydispersity index of the modified conjugated diene-based polymer falls in the above range, mixing with inorganic particles may be efficiently carried out, thus ensuring desired properties and remarkably increasing processability.

The modified conjugated diene-based polymer has a vinyl content of 10 wt % or more, preferably 15 wt % or more, and more preferably 20 to 70 wt %.

The vinyl content refers to the amount of a monomer having a vinyl group, or the amount of not 1,4-but 1,2-added conjugated diene monomer, based on 100 wt % of the conjugated diene monomer.

When the vinyl content of the modified conjugated diene-based polymer falls in the above range, the glass transition temperature of the polymer may be elevated. Thus, when such a polymer is applied to tires, the properties required of tires, such as running resistance and braking force, may be satisfied, and superior fuel economy may result.

The conjugated diene-based polymer chain, represented as P in Chemical Formula 1, may be derived from a homopolymer of a conjugated diene monomer or a copolymer of a conjugated diene monomer and a vinyl aromatic monomer.

Specifically, the conjugated diene-based polymer chain may be formed as follows: a conjugated diene monomer, or a conjugated diene monomer and a vinyl aromatic monomer, may be polymerized in a batch manner or a continuous manner using a hydrocarbon solvent in the presence of an organo-alkali metal compound, thus obtaining a homopolymer or a copolymer having an alkali metal end, which is then reacted with a silyl group substituted with at least one alkoxy group.

As such, the conjugated diene-based polymer chain may be a polymer chain comprising 0.0001 to 50 wt %, 10 to 40 wt %, or 20 to 40 wt % of the aromatic vinyl monomer, based on 100 wt % in total of the conjugated diene monomer, or the conjugated diene monomer and the vinyl aromatic monomer.

The polymer chain comprising the conjugated diene monomer and the vinyl aromatic monomer may be, for example, a random polymer chain.

The conjugated diene monomer may include at least one selected from the group consisting of 1,3-butadiene, 2,3-dimethyl-1,3-butadiene, piperylene, 3-butyl-1,3-octadiene, isoprene, and 2-phenyl-1,3-butadiene.

The vinyl aromatic monomer may include at least one selected from the group consisting of styrene, α-methylstyrene, 3-methylstyrene, 4-methylstyrene, 4-propylstyrene, 1-vinylnaphthalene, 4-cyclohexylstyrene, 4-(p-methylphenyl)styrene, and 1-vinyl-5-hexylnaphthalene. Particularly useful is styrene or α-methylstyrene.

The modified conjugated diene-based polymer may have a Mooney viscosity of 40 or more, preferably from 40 to 100, and more preferably from 45 to 90. Given the above Mooney viscosity range, a modified conjugated diene-based polymer having improved heat build-up and high processability, compatibility, tensile strength, wear resistance, fuel economy, and wet skid resistance may be prepared.

In an embodiment of the present invention, the modified conjugated diene-based polymer may be represented by Chemical Formula 2 or Chemical Formula 3 below:

Chemical Formula 2

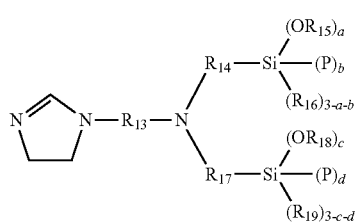

Chemical Formula 3

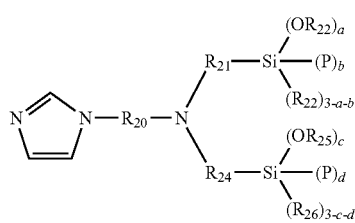

in Chemical Formulas 2 and 3, $R_{15}$, $R_{16}$, $R_{18}$, $R_{19}$, $R_{22}$, $R_{23}$, $R_{25}$, and $R_{26}$ are each independently a C1-C5 alkyl group, $R_{13}$, $R_{14}$, $R_{17}$, $R_{20}$, $R_{21}$, and $R_{24}$ are each independently a C1-C5 alkylene group, P is a conjugated diene-based polymer chain, a and c are each independently 0, 1, or 2, b and d are each independently 1, 2, or 3, and a+b and c+d are each independently 1, 2, or 3.

Also, the modified conjugated diene-based polymer may be represented by Chemical Formula 4 or Chemical Formula 5 below:

Chemical Formula 4

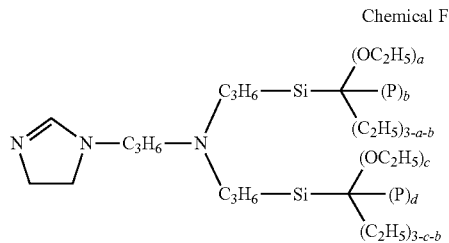

Chemical Formula 5

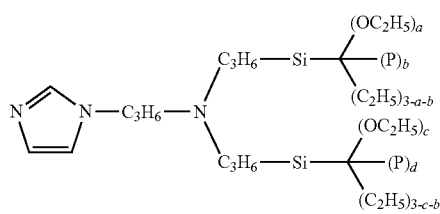

in Chemical Formulas 4 and 5, P is a conjugated diene-based polymer chain, a and c are each independently 0, 1, or 2, b and d are each independently 1, 2, or 3, and a+b and c+d are each independently 1, 2, or 3.

Specifically, the modified conjugated diene-based polymer may be represented by Chemical Formula 6 or Chemical Formula 7 below:

Chemical Formula 6

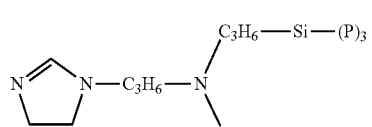

Chemical Formula 7

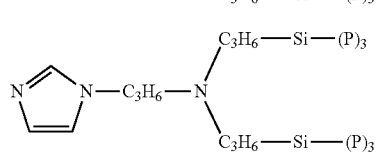

in Chemical Formulas 6 and 7, P is a conjugated diene-based polymer chain.

Another aspect of the present invention addresses a method of preparing a modified conjugated diene-based polymer, comprising: (a) polymerizing a conjugated diene monomer or a conjugated diene monomer and a vinyl aromatic monomer with an organometallic compound in the presence of a solvent, thus forming an active polymer having a metal end; and (b) modifying the active polymer with a compound represented by Chemical Formula 8 below:

[Chemical Formula 8]

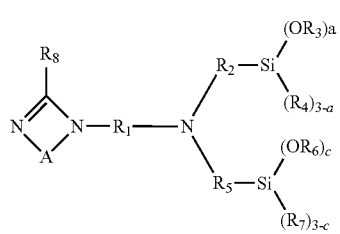

in Chemical Formula 8, $R_1$, $R_2$, and $R_5$ are each independently a C1-C10 alkylene group, $R_3$, $R_4$, $R_6$, and $R_7$ are each independently a C1-C10 alkyl group, $R_8$ is hydrogen or a C1-C10 alkyl group, a and c are each independently 0, 1, or 2, and A is

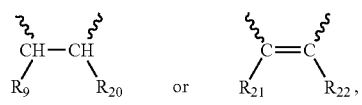

wherein $R_9$, $R_{10}$, $R_{11}$, and $R_{12}$ are each independently hydrogen or a C1-C10 alkyl group.

The conjugated diene monomer and the vinyl aromatic monomer are as described above.

The solvent is not particularly limited, so long as it may be applied in the polymerization or copolymerization of the conjugated diene monomer, and may be exemplified by a hydrocarbon, or may include at least one selected from the group consisting of n-pentane, n-hexane, n-heptane, isooctane, cyclohexane, toluene, benzene, and xylene.

The organometallic compound may be an organo-alkali metal compound, or may include at least one selected from the group consisting of an organolithium compound, an organosodium compound, an organopotassium compound, an organorubidium compound, and an organocesium compound.

For example, the organometallic compound may include at least one selected from the group consisting of methyllithium, ethyllithium, isopropyllithium, n-butyllithium, sec-butyllithium, tert-butyllithium, n-decyllithium, tert-octyllithium, phenyllithium, 1-naphthyllithium, n-eicosyllithium, 4-butylphenyllithium, 4-tolyllithium, cyclohexyllithium, 3,5-di-n-heptylcyclohexyllithium, and 4-cyclopentyllithium. Preferable as the organometallic compound is n-butyllithium, sec-butyllithium or a mixture thereof.

Alternatively, the organometallic compound may include at least one selected from the group consisting of naphthyl sodium, naphthyl potassium, lithium alkoxide, sodium alkoxide, potassium alkoxide, lithium sulfonate, sodium sulfonate, potassium sulfonate, lithium amide, sodium amide, and potassium amide, and may be used in combination with another organometallic compound.

In an embodiment of the present invention, the organometallic compound may be used in an amount of 0.01 to 10 mmol, 0.05 to 5 mmol, 0.1 to 2 mmol, or 0.1 to 1 mmol, based on 100 g in total of the monomer. When the amount of the organometallic compound falls in the above range, a conjugated diene-based polymer optimal for use in the preparation of a modified conjugated diene-based polymer may be obtained.

The molar ratio of the organometallic compound and the compound represented by Chemical Formula 8 may be, for example, 1:0.1 to 1:10, and preferably 1:0.3 to 1:2. When the molar ratio thereof falls in the above range, the conjugated diene-based polymer may be subjected to a modification reaction to ensure optimal performance.

As used herein, the active polymer having a metal end refers to a polymer comprising a polymer anion and a metal cation, which are coupled with each other.

In the method of preparing the modified conjugated diene-based polymer according to an embodiment of the present invention, the polymerizing in (a) may be performed with the additional use of a polar additive. The reason why the polar additive is further added is that the reaction rates of the conjugated diene monomer and the vinyl aromatic monomer are controlled by the polar additive.

The polar additive may be a base, or may include ether, amine or mixtures thereof. Specifically, it may be selected from the group consisting of tetrahydrofuran, ditetrahydrofurylpropane, diethylether, cyclomylether, dipropylether, ethylenedimethylether, ethylenedimethylether, diethyleneglycol, dimethylether, tert-butoxyethoxyethane bis(2-dimethylaminoethyl)ether, (dimethylaminoethyl)ethylether, trimethylamine, triethylamine, tripropylamine, and tetramethylethylenediamine, and is preferably ditetrahydropropylpropane, triethylamine, or tetramethylethylenediamine.

The polar additive may be used in an amount of 0.001 to 50 g, 0.001 to 10 g, 0.005 to 1 g, or 0.005 to 0.1 g, based on 100 g in total of the added monomer.

The polar additive may be used in an amount of 0.001 to 10 g, 0.005 to 1 g, or 0.005 to 0.1 g, based on 1 mmol in total of the added organometallic compound.

When the conjugated diene monomer and the vinyl aromatic monomer are copolymerized, it is easy to prepare a block copolymer due to the difference in the reaction rates therebetween. However, when the polar additive is added, the low reaction rate of the vinyl aromatic monomer may be increased to thus obtain the microstructure of the corresponding copolymer, for example, a random copolymer.

In (a), the polymerization may be exemplified by anionic polymerization. Specifically, the polymerization in (a) may be living anionic polymerization for forming an active end through a growth reaction by anions.

Also, the polymerization in (a) may be either high-temperature polymerization or room-temperature polymerization.

High-temperature polymerization is a polymerization process that comprises adding an organometallic compound and then applying heat to increase the reaction temperature, and room-temperature polymerization is a polymerization process that takes place in such a way that heat is not applied after the organometallic compound is added.

The polymerization in (a) may take place at a temperature ranging from −20 to 200° C., 0 to 150° C., or 10 to 120° C.

In (b), at least one, or two or three, selected from among compounds represented by Chemical Formula 8, may be added.

Also, (b) may be carried out at 0 to 90° C. for 1 min to 5 hr.

In an embodiment of the present invention, the method of preparing the modified conjugated diene-based polymer may be carried out in a batch manner, or alternatively in a continuous manner using at least one reactor.

The compound of Chemical Formula 8 may be represented by, for example, Chemical Formula 9 or Chemical Formula 10 below:

Chemical Formula 9

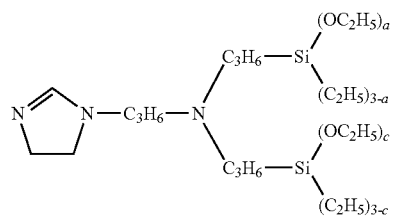

Chemical Formula 10

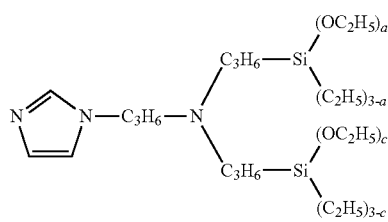

in Chemical Formulas 9 and 10, a and c are each independently 0, 1, or 2.

Also, the compound of Chemical Formula 8 may be represented by Chemical Formula 11 or Chemical Formula 12 below.

Chemical Formula 11

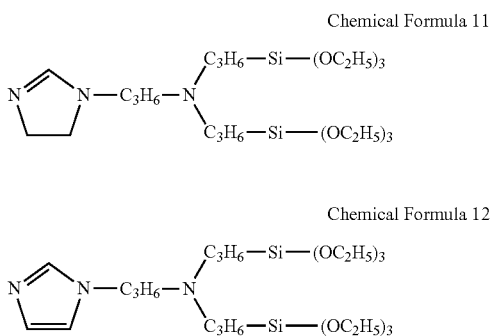

Chemical Formula 12

Still another aspect of the present invention addresses a modified conjugated diene-based polymer, prepared by the above method.

The modified conjugated diene-based polymer may be represented by Chemical Formula 1 below:

[Chemical Formula 1]

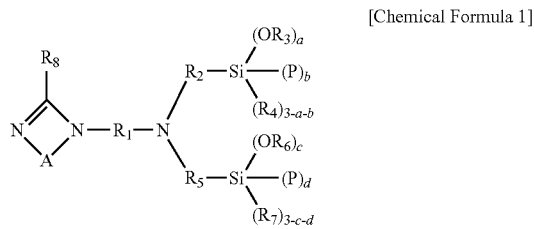

in Chemical Formula 1, $R_1$, $R_2$, and $R_5$ are each independently a C1-C10 alkylene group, $R_3$, $R_4$, $R_6$, and $R_7$ are each independently a C1-C10 alkyl group, $R_8$ is hydrogen or a C1-C10 alkyl group, P is a conjugated diene-based polymer chain, a and c are each independently 0, 1, or 2, b and d are each independently 1, 2, or 3, a+b and c+d are each independently 1, 2, or 3, and A is

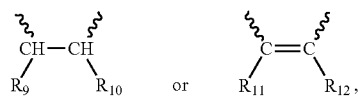

wherein $R_9$, $R_{10}$, $R_{11}$, and $R_{12}$ are each independently hydrogen or a C1-C10 alkyl group.

The modified conjugated diene-based polymer may exhibit viscoelastic properties. When measured at 10 Hz using DMA after mixing with silica, Tan δ at 0° C. may be in the range of 0.4 to 1, or 0.5 to 1. Given the above Tan δ range, desired skid resistance or wet resistance may be obtained.

Also, Tan δ at 60° C. may be in the range of 0.3 to 0.2, or 0.15 to 0.1. Given the above Tan δ range, desired rolling resistance or rotational resistance (RR) may be obtained.

Yet another aspect of the present invention addresses a modified conjugated diene-based polymer rubber composition, comprising 100 parts by weight of the modified conjugated diene-based polymer and 0.1 to 200 parts by weight of an inorganic filler.

The amount of the inorganic filler may be 10 to 150 parts by weight, or 50 to 100 parts by weight.

The inorganic filler may include at least one selected from the group consisting of a silica-based filler, carbon black, and mixtures thereof. When the inorganic filler is a silica-based filler, dispersibility is significantly increased and the end of the modified conjugated diene-based polymer of the invention may be coupled with silica particles, thus significantly decreasing hysteresis loss.

The modified conjugated diene-based polymer rubber composition may further comprise an additional conjugated diene-based polymer.

The additional conjugated diene-based polymer may include SBR (styrene-butadiene rubber), BR (butadiene rubber), natural rubber, or mixtures thereof. SBR may be exemplified by SSBR (solution styrene-butadiene rubber).

When the additional conjugated diene-based polymer is further added, the modified conjugated diene-based polymer rubber composition may comprise 20 to 100 parts by weight of the modified conjugated diene-based polymer and 0 to 80 parts by weight of the additional conjugated diene-based polymer.

Alternatively, the modified conjugated diene-based polymer rubber composition according to the present invention may comprise 20 to 99 parts by weight of the modified conjugated diene-based polymer and 1 to 80 parts by weight of the additional conjugated diene-based polymer.

Alternatively, the modified conjugated diene-based polymer rubber composition according to the present invention may comprise 10 to 100 parts by weight of the modified conjugated diene-based polymer, 0 to 90 parts by weight of the additional conjugated diene-based polymer, 0 to 100 parts by weight of carbon black, 5 to 200 parts by weight of silica, and 2 to 20 parts by weight of a silane coupling agent.

Alternatively, the modified conjugated diene-based polymer rubber composition according to the present invention may comprise 10 to 100 parts by weight of the modified conjugated diene-based polymer, 0 to 90 parts by weight of the additional conjugated diene-based polymer, 0 to 100 parts by weight of carbon black, 5 to 200 parts by weight of silica, and 2 to 20 parts by weight of a silane coupling agent, in which the total weight of the modified conjugated diene-based polymer and the additional conjugated diene-based polymer may be 100 parts by weight.

Alternatively, the modified conjugated diene-based polymer rubber composition according to the present invention may comprise 100 parts by weight of a polymer mixture comprising 10 to 99 wt % of the modified conjugated diene-based polymer and 1 to 90 wt % of the additional conjugated diene-based polymer, 1 to 100 parts by weight of carbon black, 5 to 200 parts by weight of silica, and 2 to 20 parts by weight of a silane coupling agent.

In addition, the modified conjugated diene-based polymer rubber composition may further comprise 1 to 100 parts by weight of oil. The oil may be exemplified by mineral oil or a softener.

The oil may be used in an amount of, for example, 10 to 100 parts by weight, or 20 to 80 parts by weight, based on 100 parts by weight of the conjugated diene-based copolymer. Given the above oil amount range, desired properties may be exhibited, and the rubber composition may be appropriately softened, thus increasing processability.

Still yet another aspect of the present invention addresses a modifier, which is a compound represented by Chemical Formula 8 below:

[Chemical Formula 8]

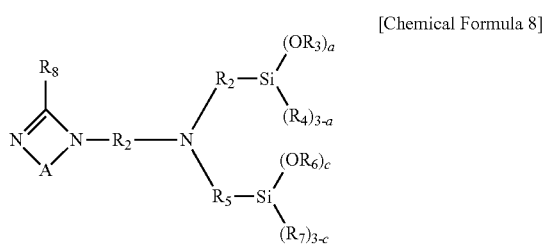

in Chemical Formula 8, $R_1$, $R_2$, and $R_5$ are each independently a C1-C10 alkylene group, $R_3$, $R_4$, $R_6$, and $R_7$ are each independently a C1-C10 alkyl group, $R_8$ is hydrogen or a C1-C10 alkyl group, a and c are each independently 0, 1, or 2, and A is

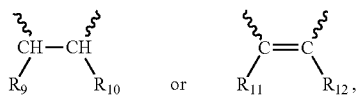

wherein $R_9$, $R_{10}$, $R_{11}$, and $R_{12}$ are each independently hydrogen or a C1-C10 alkyl group.

The compound of Chemical Formula 8 may be represented by, for example, Chemical Formula 9 or Chemical Formula 10 below:

[Chemical Formula 9]

[Chemical Formula 10]

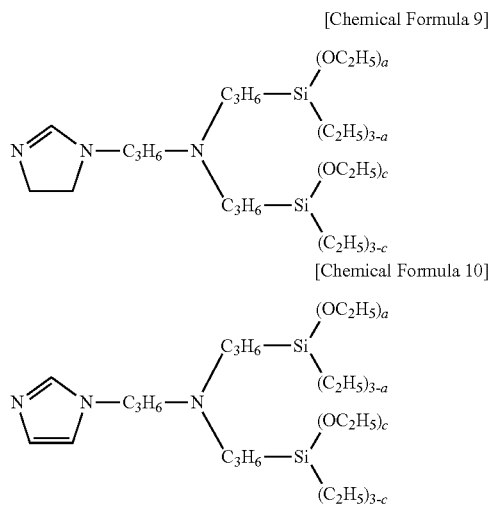

in Chemical Formulas 9 and 10, a and c are each independently 0, 1, or 2.

Also, the compound of Chemical Formula 8 may be represented by Chemical Formula 11 or Chemical Formula 12 below.

[Chemical Formula 11]

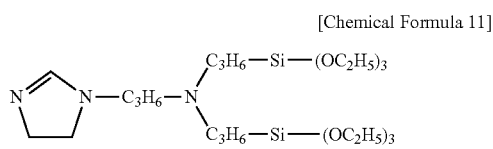

[Chemical Formula 12]

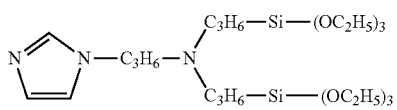

A further aspect of the present invention addresses a tire or tire tread using the modified conjugated diene-based polymer rubber composition described above.

The tire or tire tread is manufactured using the rubber composition comprising the modified conjugated diene-based polymer, which has high processability and superior compatibility with the inorganic filler, and thereby can manifest high tensile strength, wear resistance, and wet skid resistance, as well as low rolling resistance.

MODE FOR INVENTION

A better understanding of the present invention may be obtained via the following examples. However, embodiments of the present invention may be changed in various forms, and are not to be construed as limiting the scope of the present invention. The embodiments of the present invention are provided to fully describe the present invention to those having ordinary knowledge in the art to which the present invention pertains.

Example 1

270 g of styrene, 710 g of 1,3-butadiene, 5000 g of n-hexane, and 0.86 g of 2,2-bis(2-oxolanyl)propane as a polar additive were placed in a 20 L autoclave reactor, and then the temperature inside the reactor was raised to 40° C. When the temperature inside the reactor reached 40° C., 4 mmol of n-butyllithium was placed in the reactor, followed by an adiabatic heating reaction. After about 20 min, 20 g of 1,3-butadiene was added. After 5 min, 4.3 mmol of N,N-bis(triethoxysilylpropyl)aminopropyl-1-imidazole was added, and the reaction was carried out for 15 min. Then, the polymerization reaction was stopped using ethanol, and 45 mL of a solution of 0.3 wt % BHT (butylated hydroxytoluene) antioxidant in hexane was added.

The resulting polymer was placed in water warmed with steam and stirred to remove the solvent, followed by roll drying to remove the remaining solvent and water, yielding a modified conjugated diene-based polymer. The results of analysis of the modified conjugated diene-based polymer thus obtained are shown in Table 1 below.

Example 2

Three reactors were prepared. Among them, the first and second reactors were used as polymerization reactors, and the third reactor was used as a modification reactor.

Styrene, 1,3-butadiene, and n-hexane, without impurities such as water, were mixed at rates of 1.788 kg/h, 4.477 kg/h, and 4.176 kg/h, respectively, before being placed in the reactors. The resulting mixed solution was continuously fed into the first reactor. Subsequently, 2,2-bis(2-oxolanyl)propane as a polar additive and n-butyllithium were fed at rates of 3.58 g/h and 39.57 mmol/h, respectively, into the first reactor, and the temperature inside the reactor was adjusted to 70° C.

The polymer output from the first reactor was continuously fed into the upper portion of the second reactor, and a polymerization reaction was carried out while the temperature was maintained at 85° C. The polymer output from the second reactor was continuously fed into the upper portion of the third reactor, N,N-bis(triethoxysilylpropyl)aminopropyl-1-imidazole was continuously fed at a rate of 10.6 mmol/h, and a modification reaction was carried out. To the polymer output from the third reactor, a mixed solution of isopropylalcohol and an antioxidant (Wingstay-K) at 8:2 was added at a rate of 32.5 g/h to stop the polymerization reaction, thereby yielding a polymer.

100 parts by weight of the polymer thus obtained was mixed with 25 phr of TDAE oil (a distilled aromatic extract having a glass transition temperature of about −44 to about −50° C.), placed in water warmed with steam, stirred to remove the solvent, and then roll dried to remove the remaining solvent and water, yielding a modified conjugated diene-based polymer. The results of analysis of the modified conjugated diene-based polymer thus obtained are shown in Table 1 below.

Example 3

270 g of styrene, 710 g of 1,3-butadiene, 5000 g of n-hexane, and 0.86 g of 2,2-bis(2-oxolanyl)propane as a polar additive were placed in a 20 L autoclave reactor, and then the temperature inside the reactor was raised to 40° C. When the temperature inside the reactor reached 40° C., 4 mmol of n-butyllithium was placed in the reactor, followed by an adiabatic heating reaction. After about 20 min, 20 g of 1,3-butadiene was added. After 5 min, 4.3 mmol of N,N-bis(triethoxysilylpropyl)aminopropyl-1-(4,5-dihydro)imidazole, in lieu of N,N-bis(triethoxysilylpropyl)aminopropyl-1-imidazole, used in Example 1, was added, and the reaction was carried out for 15 min. Then, the polymerization reaction was stopped using ethanol, and 45 mL of a solution of 0.3 wt % BHT (butylated hydroxytoluene) antioxidant in hexane was added.

The resulting polymer was placed in water warmed with steam and stirred to remove the solvent, followed by roll drying to remove the remaining solvent and water, yielding a modified conjugated diene-based polymer. The results of analysis of the modified conjugated diene-based polymer thus obtained are shown in Table 1 below.

Example 4

360 g of styrene, 610 g of 1,3-butadiene, 5000 g of n-hexane, and 0.86 g of 2,2-bis(2-oxolanyl)propane as a polar additive were placed in a 20 L autoclave reactor, and then the temperature inside the reactor was raised to 40° C. When the temperature inside the reactor reached 40° C., 4 mmol of n-butyllithium was placed in the reactor, followed by an adiabatic heating reaction. After about 20 min, 20 g of 1,3-butadiene was added. After 5 min, 4.3 mmol of N,N-bis(triethoxysilylpropyl)aminopropyl-1-imidazole was added, and the reaction was carried out for 15 min. Then, the polymerization reaction was stopped using ethanol, and 45 mL of a solution of 0.3 wt % BHT (butylated hydroxytoluene) antioxidant in hexane was added.

The resulting polymer was placed in water warmed with steam and stirred to remove the solvent, followed by roll drying to remove the remaining solvent and water, yielding a modified conjugated diene-based polymer. The results of analysis of the modified conjugated diene-based polymer thus obtained are shown in Table 1 below.

Example 5

Three reactors were prepared. Among them, the first and second reactors were used as polymerization reactors, and the third reactor was used as a modification reactor.

Specifically, styrene, 1,3-butadiene, and n-hexane, without impurities such as water, were mixed at rates of 2.373 kg/h, 3.921 kg/h, and 4.196 kg/h, respectively, before being placed in the reactors. The resulting mixed solution was continuously fed into the first reactor. Subsequently, 2,2-bis(2-oxolanyl)propane, as a polar additive, and n-butyllithium were fed at rates of 3.58 g/h and 39.57 mmol/h, respectively, into the first reactor, and the temperature inside the reactor was adjusted to 70° C.

The polymer output from the first reactor was continuously fed into the upper portion of the second reactor, and the temperature was maintained at 85° C. The polymer output from the second reactor was continuously fed into the upper portion of the third reactor, N,N-bis(triethoxysilylpropyl)aminopropyl-1-imidazole was continuously fed at a rate of 10.6 mmol/h, and a modification reaction was carried out. To the polymer output from the third reactor, a mixed solution of isopropylalcohol and an antioxidant (Wingstay-K) at 8:2 was added at a rate of 32.5 g/h to stop the polymerization reaction, yielding a polymer.

100 parts by weight of the polymer thus obtained was mixed with 25 phr of TDAE oil (a distilled aromatic extract having a glass transition temperature of about −44 to about −50° C.), placed in water warmed with steam, stirred to remove the solvent, and then roll dried to remove the remaining solvent and water, yielding a modified conjugated diene-based polymer. The results of analysis of the modified conjugated diene-based polymer thus obtained are shown in Table 1 below.

Comparative Example 1

The results of analysis of a commercially available non-modified conjugated diene-based polymer (5025-2HM grade, made by LANXESS Deutschland GmbH) are shown in Table 2 below.

Comparative Example 2

The results of analysis of a commercially available modified conjugated diene-based polymer (TUFDENETM 3835, made by Asahi Kasei) are shown in Table 2 below. For reference, in the non-modified conjugated diene-based polymer (TUFDENETM 3835), RAE oil was used, in lieu of TDAE oil as in Example 1.

Comparative Example 3

A modified conjugated diene-based polymer was prepared in the same manner as in Example 1, with the exception that 1.2 mmol of dimethylchlorosilane, as a coupling agent, was used, instead of the N,N-bis(triethoxysilylpropyl)aminopropyl-1-imidazole. The results of analysis of the modified conjugated diene-based polymer thus obtained are shown in Table 2 below.

Comparative Example 4

A modified conjugated diene-based polymer was prepared in the same manner as in Example 1, with the exception that 4.3 mmol of N,N-bis(triethoxysilylpropyl)piperazine was used, instead of the N,N-bis(triethoxysilylpropyl)aminopropyl-1-imidazole. The results of analysis of the modified conjugated diene-based polymer thus obtained are shown in Table 2 below.

The conjugated diene-based polymers of Examples 1 to 5 and Comparative Examples 1 to 4 were analyzed through the following methods.

a) Mooney viscosity: two samples having a weight of 15 g or more were preheated for 1 min and then measured at 100° C. for 4 min using an MV-2000, made by ALPHA Technologies.

b) Styrene monomer (SM) and Vinyl content: measurement was conducted using NMR.

c) Weight average molecular weight (Mw), Number average molecular weight (Mn), and Polydispersity Index (PDI): measurement was conducted via GPC at 40° C. For this, a column was composed of a combination of two PLgel Olexis columns and one PLgel mixed-C column, made by Polymer Laboratories, and all newly replaced columns were mixed bed-type columns. Also, polystyrene (PS) was a GPC standard material for the calculation of molecular weight.

The conjugated diene-based polymer rubber compositions were prepared using, as raw rubber, samples A, B, C, D, E, F, G, and H, shown in Tables 1 and 2, under the mixing conditions of Table 3 below. The unit of material in Table 3 is phr, based on 100 parts by weight of rubber.

Specifically, the conjugated diene-based polymer rubber composition was kneaded through primary kneading and secondary kneading. Upon primary kneading, raw rubber (conjugated diene-based polymer), a filler, an organosilane coupling agent, oil, zinc oxide, a stearic acid antioxidant, an anti-aging agent, wax and an accelerator were kneaded using a Banbury mixer provided with a temperature controller. For this, the temperature of the kneader was controlled, and a first mixture was obtained at a discharge temperature of 145 to 155° C. Upon secondary kneading, the first mixture was cooled to room temperature, after which rubber, sulfur and a vulcanization accelerator were placed in the kneader,

TABLE 1

|  |  | Examples | | | | |
|---|---|---|---|---|---|---|
|  |  | High vinyl | | | High styrene | |
|  |  | 1 | 2 | 3 | 4 | 5 |
| Sample |  | A | B | C | D | E |
| n-Butyllithium (mmol) |  | 4 mmol | 39.6 | 4 mmol | 4 mmol | 39.6 |
| Polar additive (g) |  | 0.86 g | 3.58 | 0.86 g | 0.86 g | 3.58 |
| Modifier (mmol/h) | a | 4.3 mmol | 10.6 | — | 4.3 mmol | 10.6 |
|  | b | — | — | 4.3 mmol | — | — |
| Oil | Kind | — | TDAE | — | — | TDAE |
|  | phr | — | 25 | — | — | 25 |
| Mooney viscosity (MV) |  | 88 | 77 | 85 | 83 | 75 |
| NMR (%) | SM | 27 | 27 | 27 | 36 | 36 |
|  | Vinyl | 41 | 43 | 41 | 26 | 27 |
| GPC (×10$^4$) | Mp | 25 | — | 25 | 25 | — |
|  | Mn | 38 | 47 | 38 | 39 | 47 |
|  | Mw | 55 | 164 | 55 | 55 | 144 |
|  | PDI | 1.4 | 3.5 | 1.4 | 1.4 | 3.1 |

A: styrene 270 g, 1,3-butadiene 710 g, and n-hexane 5,000 g
B: styrene 1.788 kg/h, 1,3-butadiene 4.477 kg/h, and n-hexane 4.176 kg/h
C: styrene 270 g, 1,3-butadiene 710 g, and n-hexane 5,000 g
D: styrene 360 g, 1,3-butadiene 610 g, and n-hexane 5,000 g
E: styrene 2.373 kg/h, 1,3-butadiene 3.921 kg/h, and n-hexane 4.196 kg/h
a: N,N-Bis(triethoxysilylpropyl)aminopropyl-1-imidazole
b: N,N-Bis(triethoxysilylpropyl)aminopropyl-1-(4,5-dihydro)imidazole

TABLE 2

|  |  | Comparative Examples | | | |
|---|---|---|---|---|---|
|  |  | 1 | 2 | 3 | 4 |
| Sample |  | F | G | H | I |
| n-Butyllithium (mmol) |  | — | — | 4 | 4 |
| Polar additive (g) |  | — | — | 0.86 | 0.86 |
| Modifier (mmol/h) | a | — | — | 1.2 | — |
|  | b | — | — | — | 4.3 |
| Oil | Kind | TDAE | RAE | — | — |
|  | phr | 37.5 | 37.5 | — | — |
| Mooney viscosity (MV) |  | 61 | 53 | 64 | 66 |
| NMR (%) | SM | 26 | 36 | 27 | 29 |
|  | Vinyl | 50 | 26 | 43 | 41 |
| GPC (×10$^4$) | Mp | — | — | — | 25 |
|  | Mn | 39 | 33 | 31 | 34 |
|  | Mw | 69 | 94 | 50 | 45 |
|  | PDI | 1.8 | 2.8 | 1.2 | 1.3 |

F: 5025-2HM grade, made by LANXESS Deutschland GmbH
G: TUFDENE™ 3835, made by Asahi Kasei
H: styrene 270 g, 1,3-butadiene 710 g, and n-hexane 5,000 g
I: styrene 270 g, 1,3-butadiene 710 g, and n-hexane 5,000 g
c: dimethylchlorosilane
d: N,N-Bis(triethoxysilylpropyl)piperazine followed by mixing at 100° C. or less, thus obtaining a second mixture. Finally, curing was performed at 100° C. for 20 min, yielding the conjugated diene-based polymer rubber compositions of Preparation Examples 1 to 5 using, as raw rubber, the polymers of Examples 1 to 5, and of Comparative Preparation Examples 1 to 4 using the polymers of Comparative Examples 1 to 4 as raw rubber.

TABLE 3

|  | Material | Amount (unit: phr) |
|---|---|---|
| Primary kneading | Rubber | 137.5 |
|  | Silica | 70.0 |
|  | Coupling agent | 11.2 |
|  | Oil | — |
|  | Zinc oxide | 3.0 |
|  | Stearic acid | 2.0 |
|  | Antioxidant | 2.0 |
|  | Anti-aging agent | 2.0 |
|  | Wax | 1.0 |
| Secondary kneading | Rubber accelerator | 1.75 |
|  | Sulfur | 1.5 |
|  | Vulcanization accelerator | 2.0 |
|  | Total weight | 234.0 |

The properties of the prepared rubber compositions were measured through the following methods.

1) Tensile Testing

According to the tensile testing method of ASTM 412, the tensile strength upon cutting a test sample and tensile stress (300% modulus) at 300% elongation were measured. For this, a Universal Test Machine 4204, made by Instron, was used, and the tensile strength, modulus, and elongation were measured at a tensile speed of 50 cm/min at room temperature. Here, the size of the test sample is illustrated in FIG. 1.

2) Viscoelasticity

A dynamic mechanical analyzer made by TA was used. When undergoing deformation under conditions of a frequency of 10 Hz in a distortion mode and a measurement temperature (ranging from −60 to 60° C.), the Tan δ of each sample was measured. The Payne effect was represented by the difference between the minimum and the maximum in the deformation range of 0.28 to 40%. The lower the Payne effect, the higher the dispersibility of the filler such as silica. When Tan δ at 0° C., which is a low temperature, was increased, wet skid resistance became superior, and when Tan δ at 60° C., which is a high temperature, was decreased, hysteresis loss was reduced, resulting in low rolling resistance of tires, and concomitantly increased fuel economy. Table 4 below shows the properties of the vulcanized rubber.

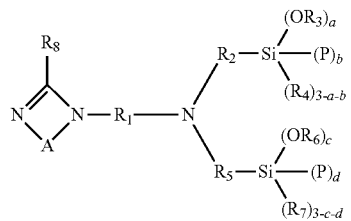

[Chemical Formula 1]

in Chemical Formula 1, $R_1$, $R_2$, and $R_5$ are each independently a C1-C10 alkylene group, $R_3$, $R_4$, $R_6$, and $R_7$ are each independently a C1-C10 alkyl group, $R_8$ is hydrogen or a C1-C10 alkyl group, P is a conjugated diene-based polymer chain, a and c are each independently 0, 1, or 2, b and d are each independently 1, 2, or 3, a+b and c+d are each independently 1, 2, or 3, and A is

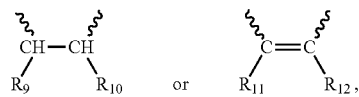

TABLE 4

|  | Test. Ex. 1 | Test. Ex. 2 | Test. Ex. 3 | Test. Ex. 4 | Test. Ex. 5 | C.Test. Ex. 1 | C.Test. Ex. 2 | C.Test. Ex. 3 | C.Test. Ex. 4 |
|---|---|---|---|---|---|---|---|---|---|
| Sample | Prep. Ex. 1 | Prep. Ex. 2 | Prep. Ex. 3 | Prep. Ex. 4 | Prep. Ex. 5 | C.Prep. Ex. 1 | C.Prep. Ex. 2 | C.Prep. Ex. 3 | C.Prep. Ex. 4 |
| 300% Modulus (Kgf/cm$^2$) | 132 | 122 | 130 | 130 | 117 | 98 | 105 | 104 | 127 |
| Tensile strength (Kgf/cm$^2$) | 213 | 193 | 202 | 203 | 187 | 161 | 177 | 168 | 161 |
| Tanδ at 0° C. | 0.967 | 0.915 | 0.902 | 0.978 | 0.917 | 0.647 | 0.766 | 0.542 | 0.803 |
| Tanδ at 60° C. | 0.101 | 0.108 | 0.106 | 0.110 | 0.119 | 0.133 | 0.142 | 0.115 | 0.109 |
| ΔG' at 60° C. (Payne Effect) | 0.29 | 0.30 | 0.30 | 0.29 | 0.31 | 0.56 | 0.45 | 0.74 | 0.35 |

As is apparent from the results of Table 4, the modified conjugated diene-based polymer rubber compositions of Preparation Examples 1 to 3 according to the present invention were significantly increased in 300% modulus (tensile stress) and tensile strength, compared to Comparative Preparation Examples 1, 3 and 4, and also exhibited low Tan δ at 60° C. Thus, when the modified conjugated diene-based polymer rubber composition according to the present invention was used in a tire, rolling resistance was decreased, whereby superior fuel efficiency resulted.

Also, the conjugated diene-based polymer rubber compositions of Preparation Examples 4 and 5 according to the present invention exhibited high Tan δ at 0° C., compared to Comparative Preparation Example 2. Thus, when the modified conjugated diene-based polymer rubber composition of the invention was used in a tire, high wet skid resistance resulted.

Also, the modified conjugated diene-based polymer rubber compositions of Preparation Examples 1 to 5 according to the present invention exhibited quite low ΔG' at 60° C., compared to Comparative Preparation Examples 1 to 4, thus significantly increasing silica dispersibility.

The invention claimed is:

1. A modified conjugated diene-based polymer represented by Chemical Formula 1 below:

wherein $R_9$, $R_{10}$, $R_{11}$, and $R_{12}$ are each independently hydrogen or a C1-C10 alkyl group, wherein the modified conjugated diene-based polymer is prepared by a method comprising:

(a) polymerizing a conjugated diene monomer, or a conjugated diene monomer and a vinyl aromatic monomer, with an organometallic compound using a solvent to form an active polymer having a metal end; and (b) modifying the active polymer with a modifier represented by Chemical Formula 8, Chemical Formula 11 or Chemical Formula 12 below:

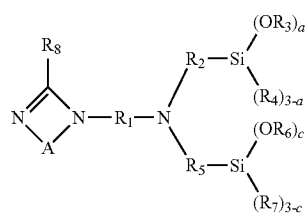

[Chemical Formula 8]

[Chemical Formula 11]

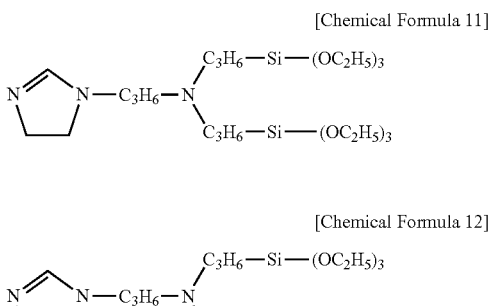

[Chemical Formula 12]

in Chemical Formula 8, $R_1$, $R_2$, and $R_5$ are each independently a C1-C10 alkylene group, $R_3$, $R_4$, $R_6$, and $R_7$ are each independently a C1-C10 alkyl group, $R_8$ is hydrogen or a C1-C10 alkyl group, a and c are each independently 1 or 2, and A is

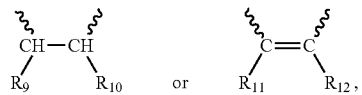

wherein $R_9$, $R_{10}$, $R_{11}$, and $R_{12}$ are each independently hydrogen or a C1-C10 alkyl group.

2. The modified conjugated diene-based polymer of claim 1, wherein Chemical Formula 1 is represented by Chemical Formula 2 or Chemical Formula 3 below:

[Chemical Formula 2]

[Chemical Formula 3]

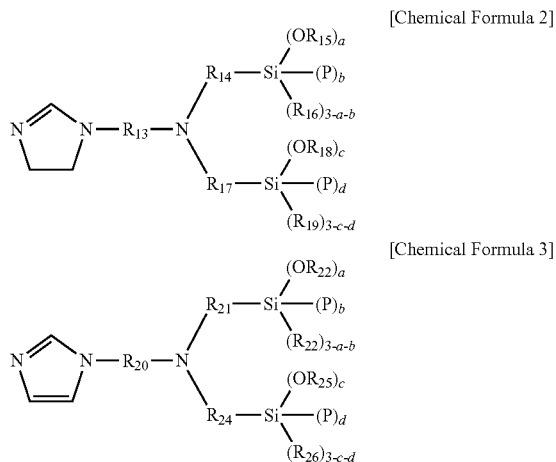

in Chemical Formulas 2 and 3, $R_{15}$, $R_{16}$, $R_{18}$, $R_{19}$, $R_{22}$, $R_{23}$, $R_{25}$, and $R_{26}$ are each independently a C1-C5 alkyl group, $R_{13}$, $R_{14}$, $R_{17}$, $R_{20}$, $R_{21}$, and $R_{24}$ are each independently a C1-C5 alkylene group, P is a conjugated diene-based polymer chain, a and c are each independently 0, 1, or 2, b and d are each independently 1, 2, or 3, and a+b and c+d are each independently 1, 2, or 3.

3. The modified conjugated diene-based polymer of claim 1, wherein Chemical Formula 1 is represented by Chemical Formula 4 or Chemical Formula 5 below:

[Chemical Formula 4]

[Chemical Formula 5]

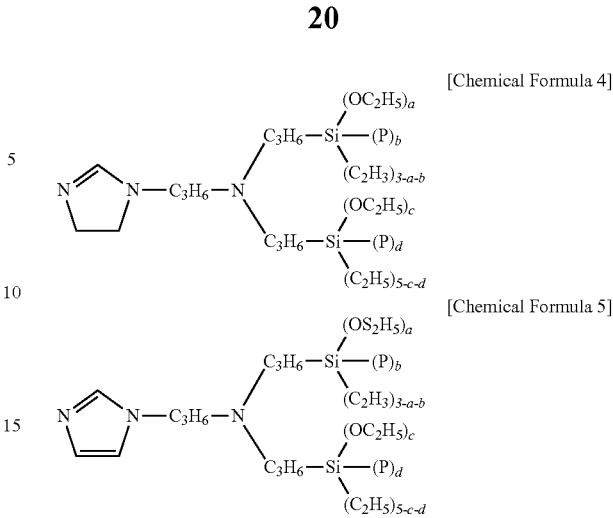

in Chemical Formulas 4 and 5, P is a conjugated diene-based polymer chain, a and c are each independently 0, 1, or 2, b and d are each independently 1, 2, or 3, and a+b and c+d are each independently 1, 2, or 3.

4. The modified conjugated diene-based polymer of claim 1, wherein the modified conjugated diene-based polymer has a number average molecular weight (Mn) of 1,000 to 2,000,000 g/mol.

5. The modified conjugated diene-based polymer of claim 1, wherein the modified conjugated diene-based polymer has a polydispersity index (Mw/Mn) of 0.5 to 10.

6. The modified conjugated diene-based polymer of claim 1, wherein the modified conjugated diene-based polymer has a vinyl content of 10 wt % or more.

7. The modified conjugated diene-based polymer of claim 1, wherein the conjugated diene-based polymer chain is derived from a homopolymer of a conjugated diene monomer or a copolymer of a conjugated diene monomer and a vinyl aromatic monomer.

8. The modified conjugated diene-based polymer of claim 1, wherein the modified conjugated diene-based polymer includes 0.0001 to 50 wt % of an aromatic vinyl monomer based on 100 wt % in total of a conjugated diene monomer and the aromatic vinyl monomer.

9. A method of preparing a modified conjugated diene-based polymer represented by Chemical Formula 1:

[Chemical Formula 1]

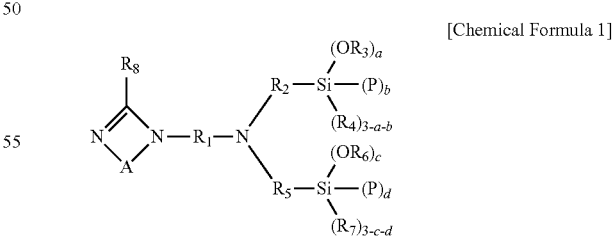

in Chemical Formula 1, $R_1$, $R_2$, and $R_5$ are each independently a C1-C10 alkylene group, $R_3$, $R_4$, $R_6$, and $R_7$ are each independently a C1-C10 alkyl group, $R_8$ is hydrogen or a C1-C10 alkyl group, P is a conjugated diene-based polymer chain, a and c are each independently 0, 1, or 2, b and d are each independently 1, 2, or 3, a+b and c+d are each independently 1, 2, or 3, and A is

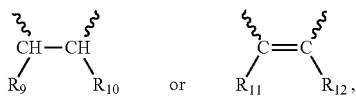

wherein $R_9$, $R_{10}$, $R_{11}$, and $R_{12}$ are each independently hydrogen or a C1-C10 alkyl group,
wherein the method comprises:
(a) polymerizing a conjugated diene monomer, or a conjugated diene monomer and a vinyl aromatic monomer, with an organometallic compound using a solvent, thus forming an active polymer having a metal end; and
(b) modifying the active polymer with a compound represented by Chemical Formula 8, Chemical Formula 11 or Chemical Formula 12 below:

[Chemical Formula 8]

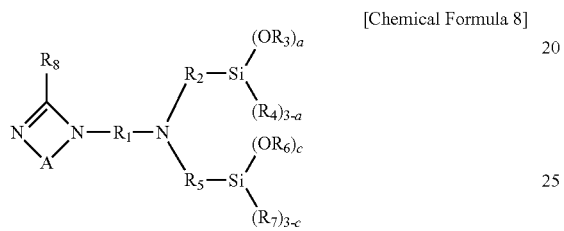

[Chemical Formula 11]

[Chemical Formula 12]

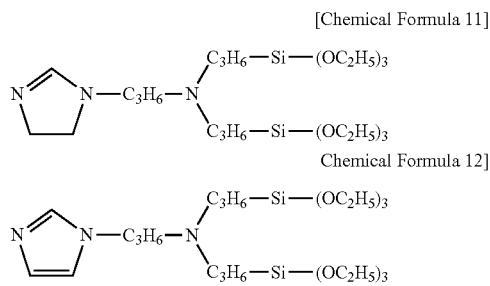

in Chemical Formula 8, $R_1$, $R_2$, and $R_5$ are each independently a C1-C10 alkylene group, $R_3$, $R_4$, $R_6$, and $R_7$ are each independently a C1-C10 alkyl group, $R_8$ is hydrogen or a C1-C10 alkyl group, a and c are each independently 1 or 2, and A is

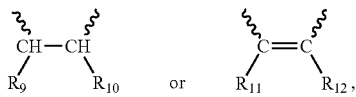

wherein $R_9$, $R_{10}$, $R_{11}$, and $R_{12}$ are each independently hydrogen or a C1-C10 alkyl group.

10. The method of claim 9, wherein Chemical Formula 8 is represented by Chemical Formula 9 or Chemical Formula 10 below:

[Chemical Formula 9]

[Chemical Formula 10]

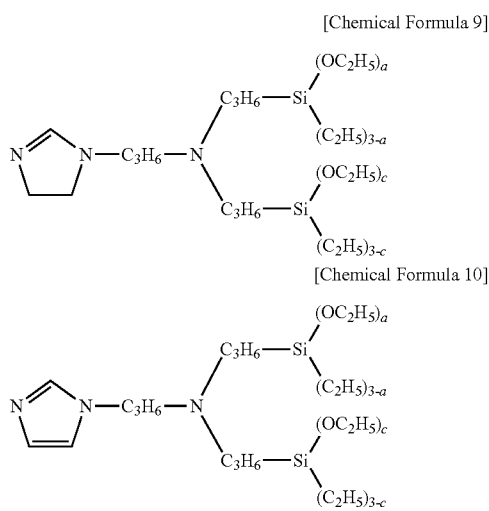

in Chemical Formulas 9 and 10, a and c are each independently 0, 1, or 2.

11. The method of claim 9, wherein the organometallic compound is used in an amount of 0.01 to 10 mmol based on 100 g in total of the monomer.

12. The method of claim 9, wherein a molar ratio of the organometallic compound and the compound represented by Chemical Formula 8 is 1:0.1 to 1:10.

13. The method of claim 9, wherein the polymerizing in (a) is performed with additional use of a polar additive.

14. The method of claim 13, wherein the polar additive is added in an amount of 0.001 to 10 g based on 1 mmol in total of the organometallic compound.

15. A modified conjugated diene-based polymer rubber composition, comprising 100 parts by weight of the modified conjugated diene-based polymer of claim 1 and 0.1 to 200 parts by weight of an inorganic filler.

16. The modified conjugated diene-based polymer rubber composition of claim 15, wherein the inorganic filler comprises at least one selected from the group consisting of a silica-based filler, carbon black, and mixtures thereof.

17. A tire or tire tread, comprising the modified conjugated diene-based polymer rubber composition of claim 15.

* * * * *